United States Patent [19]

Cohen et al.

[11] Patent Number: 4,713,384
[45] Date of Patent: Dec. 15, 1987

[54] SELECTIVE METHOD FOR BLOCKING 5HT$_2$ RECEPTORS

[75] Inventors: Marlene L. Cohen; Ray W. Fuller; William L. Garbrecht, all of Indianapolis; Kathleen R. Whitten, Zionsville, all of Ind.

[73] Assignee: Eli Lilly and Company, Indianapolis, Ind.

[21] Appl. No.: 782,338

[22] Filed: Oct. 1, 1985

[51] Int. Cl.$^4$ .................. A61K 31/48; C07D 457/04
[52] U.S. Cl. ........................................ 514/288; 546/69
[58] Field of Search ........................... 546/67, 68, 69; 514/288

[56] References Cited

U.S. PATENT DOCUMENTS

| | | | |
|---|---|---|---|
| 3,113,133 | 12/1963 | Hofmann et al. | 260/285.5 |
| 3,183,234 | 5/1965 | Garbrecht et al. | |
| 3,228,941 | 1/1966 | Bernardi et al. | 260/285.5 |
| 3,249,617 | 5/1966 | Hofmann et al. | 260/285.5 |
| 3,580,916 | 5/1971 | Garbrecht | 260/285.5 |
| 4,230,859 | 10/1980 | Rucman | 546/69 |
| 4,563,461 | 1/1986 | Cohea et al. | 546/69 |

FOREIGN PATENT DOCUMENTS 122044 10/1984 European Pat. Off. .

OTHER PUBLICATIONS

Cohen, *Drug Developement Res.*, 5, 313, (1985), (Cohen IV).
Cohen et al., *J.P.E.T.*, 232, 770, (1985), (Cohen III).
Berde, *The Medical Journal of Australia*, Special Supplement, Nov. 4, 1978, pp. 3–13.
Fanciullacci et al., *Headache*, 16, 226, (1976).
Calesnick, *AFP*, 25, 228, (1982).
Awouters, 5-Hydroxytryptamine in Perpheral Reactions (Raven Press, N.Y., 1982), pp. 71–75.
Aellig, *Eur. J. Clin. Pharm.*, 25, 759, (1983).
Sulman et al., *Headache*, 17, 203, (1979).
Amano et al., ibid, 22, 249, (1982).
Cohen et al., *J.P.E.T.*, 227, 327, (1983), (Cohen I).
Lance, *Brit. Med. J.*, 1970, (2), 327, (Lance I).
Saxena, ibid, 12, 44, (1972).
Lance and Anthony, *Proc. Aust. Assoc. Neurol.*, 7, 32, (1970).
Prusinski et al., *Pol. J. Pharmacol. Pharm.*, 37, Suppl. 189-193.
Harriet F. Lemberger et al., *Life Sci.*, 35, 71, (1984).
Hingten et al., Soc. for Neuroscience Abstract, 374, p. 125, (1983).

*Primary Examiner*—Donald G. Daus
*Assistant Examiner*—Cecilia Shen
*Attorney, Agent, or Firm*—Bruce J. Barclay; Leroy Whitaker

[57] ABSTRACT

Method of blocking 5HT without effect on alpha receptors with 1-loweralkyl-6-straight chain alkyl-8β-hydroxycycloalkyloxycarbonylergolines.

2 Claims, No Drawings

SELECTIVE METHOD FOR BLOCKING 5HT₂ RECEPTORS

BACKGROUND OF THE INVENTION

Garbrecht, U.S. Pat. No. 3,580,916 discloses a group of lysergic and 9,10-dihydrolysergic acid esters formed with various open chain and cyclic diols. The following structures summarize the disclosure in Garbrecht.

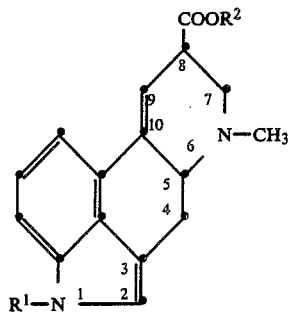

I and

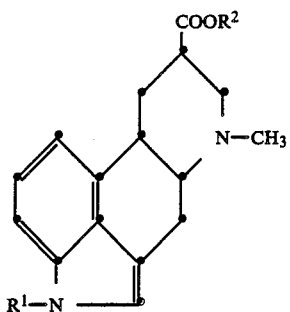

II wherein $R^2$ is H, $C_{1-3}$ alkyl, allyl or benzyl and $R^2$ is $C_2$-$C_8$ monohydroxyalkyl, $C_{2-8}$ dihydroxyalkyl or $C_{5-11}$ monohydroxycycloalkyl having from 5–8 ring carbons. The compounds are useful as serotonin antagonists, the patent stating that "In animals, the compounds act as neurosedatives . . . and are therefore useful in calming . . . animals".

The $R^2$ group in I or II when it is hydroxycycloalkyl is formed by the reaction of a dihydroxycycloalkane with an "activated" form of lysergic or dihydrolysergic acid. The following list of illustrative cycloalkyldiols is from Garbrecht.
cyclopentane-1,3-diol,
cyclohexane-1,4-diol,
5,5-dimethylcyclohexane-1,3-diol,
2-ethylcyclopentane-1,3-diol,
cycloheptane-1,2-diol,
4-methylcycloheptane-1,2-diol,
cyclooctane-1,5-diol,
3-ethylcyclooctane-1,3-diol,
4-isopropylcycloheptane-1,2-diol,
3-propylcyclooctane-1,5-diol,
3-isopropylcyclooctane-1,5-diol No compound in which $R^2$ is $C_{5-11}$ monohydroxyalkyl was actually prepared.

Recently, interest in the Garbrecht compounds was intensified by the finding that they had excellent peripheral serotonin antagonist activity against 5HT₂ receptors, at the same time and at comparable dose levels lacking any activity, agonist or antagonist, with other receptors, particularly alpha₁ receptors.

The most interesting compound was 1-isopropyl-6-methyl-8β-(1-methyl-2-hydroxy)propoxycarbonyl-5R-ergoline in which in II $R^1$ is isopropyl and $R^2$ is 1-methyl-2-hydroxypropyl. 5R refers to the orientation of the C-5 hydrogen. The C-10 hydrogen is alpha--10R, and the beta orientation at C-8 is the same as in lysergic and 9,10-dihydrolysergic acid (R). Both these acids have a 6-methyl group. An alternate name for the above compound is 1-isopropyl-9,10-dihydrolysergic acid 1-methyl-2-hydroxypropyl ester.

Cohen et al. *J.P.E.T.*, 227, 327 (1983) (Cohen I) reported that the above compound, given the code number LY53857, was a potent antagonist of vascular contraction to serotonin, which effect is mediated by 5HT₂ receptors. The compound had minimal affinity for vascular alpha adrenergic, dopaminergic and histaminergic receptors ($K_{dissoc.} \approx 10^{-10}$ vs $\sim 10^{-5}$). Other papers on the pharmacologic properties of LY53857 include Cohen et al, *J.P.E.T.*, 232, 770 (1985) (Cohen III); Harriet Lemberger et al., *Life Sciences*, 35, 71 (1984); Cohen, *Drug Development Res.*, 5, 313 (1985), (Cohen IV). Cohen and Fuller, EPO 122,044, published 10-17-84 (Cohen V) covers the use of the open chain hydroxy alkyl esters of 1-alkyl-dihydrolysergic acid as peripheral 5HT₂ receptor antagonists.

The above articles tend to be cumulative concerning the lack of effect of LY53857 on receptors other than 5HT₂ receptors, particularly peripheral alpha₂ receptors.

Among the other prior art references, the next most pertinent group is that which contains references which have a bearing on the problem of finding selective ergolines (those with only one agonist or antagonist receptor interaction), including the following references:

Berde, *The Medical Journal of Australia* Special Supplement, page 3 (1978), divides the ergot alkaloids into four groups on structural grounds. Table 1 on page 4 of this article illustrates again the great differences in pharmacological activity between the various ergot alkaloids, specifically those listed at the top of the Table. The lack of selectivity of these alkaloids is fully illustrated; each has multiple pharmacologic activities. Attention is particularly called to page 6 of Berde where there is a section entitled "Use in Migraine". This section discusses the uses of ergotamine and methysergide in the treatment of an on-going migraine and as a preventative. Of all the compounds in Table 1, page 6 only methysergide has a 1,000 (most active compound rating) in a single test (5HT receptor blockade). The lack of correlation between these activities and migraine treatment become apparent when one realizes that ergotamine, the drug of choice in treating migraine, is the most active compound only in pressor and emetic activity, and not in 5HT antagonism.

Fanciullaci et al., *Headache*, 16 226 (1974), finds that both ergotamine and methysergide are 5HT agonists at low concentrations but antagonistic at higher concentrations. The authors conclude that methysergide and ergotamine therapy of migraine is not anti-serotoninergic.

Calesnick et al., *A.F.P.*, 125, 228 (1982), also concludes that serotonin receptor agonists are the most effective agents for the treatment of migraine.

Awouters writing in *5-Hydroxy Tryptamines in Peripheral Reactions*, (Raven Press, N.Y., 1982) points out that the 5HT₂ agonist activity of methysergide is responsible for some of the side effects encountered with the use of that drug. Attention is also called to page 74, last paragraph, wherein the author states that "... there is still much room for the development of compounds which specfically block 5-hydroxy tryptamine-induced responses at low doses and do not have intrinsic 5-hydroxy tryptamine-like actions at all".

The following references are in our view, less pertinent than the previous references as regards the use of ergolines in migraine, and to the role of serotonin in that disease.

Aellig, *Euro. J. Clin. Pharm.*, 25, 759 (1983) describes experiments contrasting pizotifen (pizotyline—a tricyclic compound having a benzene and a thiophene ring attached to a central cycloheptane carrying a 4-N-methylpiperidine—presently on clinical trial for migraine) with ergotamine in producing vasoconstriction, with or without noradrenaline. The conclusion is that ergotamine and noradrenaline act together to constrict cranial arteries when ergotamine is given for a migraine attack.

Sulman, *Headache*, 17, 203 (1977) discusses the use of danitracene in preventing migraine attacks. The drug had antiserotonin, antihistamine and antidepressive affects. Side affects attributable to the drug are given in Table 5.

Amano, ibid, 22, 249 (1982) studied the cerebrovascular changes in patients with headache being treated with the antiserotonin drugs, methysergide and cyproheptadine (compound 6 page 203 of Sulman). The author concludes that administration of methysergide may result in stimulation of serotonergic receptors, although it is also an antiserotonin drug.

Lance et al., *Brit. Med. J.*, 1970 (2) 237 (Lance I) describes a comparative clinical trial of five serotonin antagonists in migraine. Improvement rates were (Table 1): methysergide 64%, cyproheptadine 43%, placebo 32%, lysenyl 34%, methdilazine 45% and BC105 50%. The side effects were very high (Table 2). 24–35% (placebo only 12%). Lysenyl is N-D-6-methylisoergolenyldiethylcarbamide—diethylamide of isolysergic acid. The difference in improvement rate between it and methysergide, another ergoline carboxamide, again points out the fact that all ergolines are not alike. Vasoconstriction was one of the chief side effects of methysergide treatment. The occurrence of retroperitoneal fibrosis etc. as a methysergide side effect is discussed.

Saxena, ibid, 12 44 (1972) concludes that "[t]he results of the present study cast doubts on the assumption that the antimigraine drugs owe their therapeutic activity to their antiserotonin actionp". (Page 52). He believes that selective vasoconstriction is the key to the treatment of migraine.

Lance and Anthony, *Proc. Aust. Assoc. Neurol.*, 7, 31 (1970) (Lance II) contains an expansion of the data in Lance I. The authors conclude that the effectiveness of antiserotonin agents in migraine depends on their exerting a serotonin agonist action in promoting arterial vasoconstriction.

Prusinski et al., *Pol. J. Pharmacol. Pharm.*, 27, (Supp) 189 (1975) tested two antiserotonin drugs (neither an ergoline) in migraine. Both were 64% effective.

Four additional patents are being cited as examples of ergolines with a substituent on the indole nitrogen. U.S. Pat. No. 3,113,133, Hofmann et al., discloses and claims esters and amides carrying an indole N substituent such as a lower alkyl or alkenyl group or an aralkyl group. The compounds are said to be useful as serotonin antagonists, in treating inflammatory, arthritic and allergic diseases and in treating carcinoid syndrome.

U.S. Pat. No. 3,249,617, Hofman et al., covers (indole) N-alkyl or allyl lysergic acids, useful as intermediates.

U.S. Pat. No. 3,228,941, Bernardi et al., discloses and claims a group of (indole) N-methylergolines—amides, hydroxamides and amidines. The compounds are alleged to have oxytocic, adrenolytic, hypotensive, sedative and antienteraminic action.

U.S. Pat. No. 4,230,859 to Rucman discloses dihydrolysergic acid carrying a $C_{1-5}$ alkyl group on the indole nitrogen useful as intermediates.

Finally ergolines actually used in the treatment of migraine include ergotamine, methysergide and ergonovine. Ergotamine is both a partial alpha-agonist and an alpha-antagonist. In the peripheral and central nervous systems, it is mainly an antagonist, but is a partial agonist in certain blood vessels. Ergonovine, sometimes used in the treatment of migraine, is a 5HT agonist, is a selective and fairly potent 5HT antagonist in smooth muscle, is a weak dopaminergic antagonist, and is a highly active 5HT antagonist in the uterus. Methysergide, sometimes used in migraine, has no oxytocic action, little or no action on alpha-receptors, but is a partial 5HT agonist in certain blood vessels and a very potent 5HT antagonist in the CNS. From a description of their properties, it is apparent that none of these is an ideal migraine drug.

SUMMARY OF THE INVENTION

This invention provides a method of blocking $5HT_2$ receptors without effect on alpha receptors which comprises administering to a mammal having an excess of serotonin centrally or peripherally a $5HT_2$ blocking dose, which dose does not affect alpha receptors, of an ergoline of the formula:

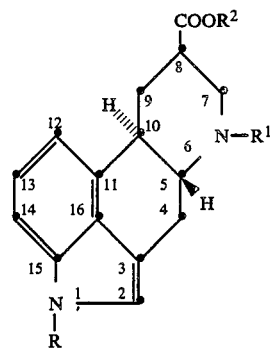

III wherein R is primary or secondary $C_{1-8}$ alkyl, $CH_2-C_{2-4}$ alkenyl, $C_{3-8}$ cycloalkyl or $C_{3-6}$ cycloalkyl-substituted $C_{1-5}$ primary or secondary alkyl, the total number of carbon atoms in R not to exceed 8; $R^1$ is allyl or $C_{1-4}$ straight-chain alkyl; ie; methyl, ethyl, n-propyl or n-butyl; and $R^2$ is hydroxy-substituted $C_{5-7}$ cycloalkyl, and pharmaceutically acceptable acid addition salts thereof.

Groups which R in the above formula represent include methyl, ethyl, allyl, n-propyl, isopropyl, crotyl, methallyl, n-hexyl, sec-amyl, sec-octyl, n-heptyl, 2,4-dimethylpentyl, 2-ethylpentyl, cyclopropyl, cyclopropylmethyl, cyclopentyl methyl, 2-cyclobutyl ethyl, cyclohexyl, isobutyl, sec.-butyl, 3-methyl-2-butyl isoamyl, 2-methylhexyl, 3-methylhexyl, 4-methylhexyl- (isohexyl), 2-hexyl, 3-hexyl n-heptyl, 2-heptyl, 3-heptyl, 4-heptyl, n-octyl, 2-octyl, 3-octyl, 4-octyl isooctyl, 2-methylheptyl, 3-methyl-2-heptyl, and the like. Illustrative of the groups which $R^2$ represents include 4-hydroxycyclohexyl, 3-hydroxycyclohexyl, 3-hydroxycyclopentyl, 3-hydroxycycloheptyl, 4-hydroxycycloheptyl, 2-hydroxycyclopentyl, 2-hydroxycyclohexyl, 2-hydroxycycloheptyl and the like.

Compounds according to the above formula III can be named as ergoline derivatives in which the trans($-$) or 5R,10R configuration of the bridgehead hydrogens is specified (The same configuration as in the naturally-occurring ergot alkaloids). In U.S. Pat. No. 3,580,916, a different naming system was used; the basic ring system is a 6aR,10aR-4,6,6a,7,8,9,10,10a-octahydroindolo[4,3-fg]quinoline. We prefer to use the trivial name "ergoline" with the numbering system specified in I above when $R^1$ is other than methyl. When $R^1$ is methyl, we prefer to use the 9,10-dihydrolysergic acid nomenclature. Illustratively, 9,10-dihydrolysergic acid is 6aR,10aR-7-methyl-4,6,6a,7,8,9,10,10a-octahydroindolo[4,3-fg]quinoline-9β-carboxylic acid or 6-methyl-8β-carboxyergoline.

Pharmaceutically-acceptable acid addition salts of the compounds of formula III useful in the process of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenyl-butyrate, citrate, methanesulfonate, propanesulfonate, naphthalene-1-sulfonate, naphthalene-2-sulfonate and the like salts.

Those useful in the therapeutic processes of this invention include:

2-Hydroxycyclohexyl 1-methyl-8β-9,10-dihydrolysergate succinate

2-Hydroxycyclopentyl 1,6-diethylergoline-8β-carboxylate hydrochloride

2-Hydroxycycloheptylergoline 1-n-propyl-6-allyl-8β-carboxylate sulfate

2-Hydroxycyclohexyl 1-isopropyl-6-n-propylergoline-8β-carboxylate hydrobromide

4-Hydroxycycloheptyl 1-allyl-6-ethylergoline-8β-carboxylate tartrate and the like.

While the configuration at asymmetric carbons 5,8 and 10 in formula III is set (5β,8β and 10α), the cycloalkane diols each have two additional asymmetric carbons. For example, cyclohexane-1,3-diol should exist as two racemates, each racemate containing two enantiomers or stereoisomers. However, it is possible to draw a plane of symmetry through the cis isomer of the molecule (C-2 to C-5), thus producing a meso form in which two of the isomers are superimposable. Thus, certain of the diols used to form the esters of this invention exist as a racemate and a meso form. However, when an optically-active group is attached to one of the hydroxyls, such as a dihydrolysergic acid group, to form an ester, a plane of symmetry can no longer be drawn and the mono esters of cyclopentanediols, cyclohexanediols and cycloheptanediols will ordinarily each exist as two ($\pm$) diastereoisomeric pairs. However, with certain diols such as cyclohexane-1,4-diol, two planes of symmetry can be drawn, indicated by the dotted lines in formula IV

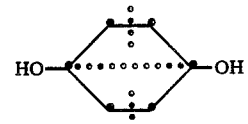

and the compounds exist as two meso forms; ie, both sets of mirror images are superimposable. However, two geometric isomers exist designated as the cis form and the trans form drawn for convenience in two dimensions as IVa and IVb.

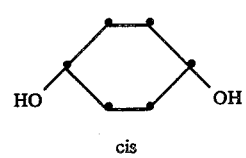

cis

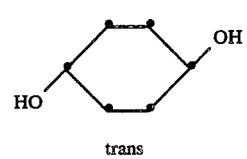

trans

When monoesters with 9,10-dihydrolysergic acid are formed, although each ester could theoretically exist in two diastereoisomeric forms, an inspection of the models indicates that such is not the case and that only two non optically-active esters exist. These will be named as the cis or trans isomer. (For a more detailed explanation of the stereochemistry of cycloalkane-1,4-diols, see "Conformational Theory" by Michael Hanach. (Academic Press, Inc., Fifth Avenue, New York, N.Y. 10003, 1965).

This invention contemplates the use of all such stereoisomeric or geometric forms represented by II above as peripheral serotonin antagonists, including mixtures or racemates. Where an individual stereoisomer or geometric isomer of a pair has one or more unexpected properties not shared by the other member of the pair, these unobviously superior isomers as such provide a second aspect of this invention.

The preparation of compounds represented by formula I above is detailed in U.S. Pat. No. 3,580,916, issued May 25, 1971.

According to this procedure, dihydrolysergic acid is first alkylated in the indole nitrogen using standard procedures,—base plus an alkyl halide. Liquid ammonia is a convenient solvent with sodamide as the base and methyl, ethyl, isopropyl or n-propyl iodide or allyl chloride or bromide as the alkylating agent. See U.S. Pat. No. 3,183,234-Garbrecht and Lin which contains general directions and a specific example of this alkylation procedure).

Alternatively, however, we prefer to employ the procedure of Marzoni, Ser. No. 782,339 filed this even date, whereby 9,10-dihydrolysergic acid is reacted with an aryl sulfonate, R—O—SO$_2$—phenyl—Y where R has its previous meaning and Y is CH$_3$, NO$_2$ or Br, in the presence of an alkali metal hydroxide in an aprotic solvent, conveniently NaOH in DMF, to yield the desired N-1 derivative.

With the indole nitrogen substituent in place, if 9,10-dihydrolysergic acid was the starting material, the next step in the synthetic procedure is esterification. This procedure requires heating; i.e., preferably at about 120° C., but the reaction is an otherwise standard acid-catalyzed esterification. The free acid and cycloalkanediol are used and the work-up of the esterification mixture involves partioning between water and a water-immiscible solvent; (CH$_2$Cl)$_2$ for example.

If it is desired to prepare a product in which the 6-methyl of the dihydrolysergic acid series is replaced by ethyl, n-propyl, n-butyl or allyl, the replacement of the 6-methyl group must take place after N$^1$-alkylation, using an ester (preferably a C$_{1-2}$ lower allyl ester as the substrate. Replacement of the 6-methyl with ethyl, n-propyl, alkyl, n-butyl or the like, can conveniently be carried out by the procedure of Kornfeld and Bach, U.S. Pat. No. 4,166,182, whereby the N-methyl is reacted with cyanogen bromide to form an N-cyano derivative. The cyano group is removed by hydrogenation using zinc dust and hydrochloric acid. The resulting product is an N$^1$-alkylergoline-8$\beta$-carboxylic acid which is a secondary amine. The desired ester group is now prepared, using the standard reaction conditions with an R$^2$OH. The secondary amine can then be alkylated or allylated in DMF solution in the presence of a base such as sodium carbonate to form a 1-alkyl (or allyl)-6-substituted ergoline-8$\beta$-carboxylic acid ester. It might seem redundant to realkylate the above secondary amine with methyl iodide since the N-methyl group was present in the starting material. It should be pointed out, however, that a methyl group containing isotopic or radioactive C or H could be inserted to give a derivative useful in metabolic studies.

The preparation of the 4-hydroxycyclohexyl ester of 1-isopropyl-6-methylergoline-8$\beta$-carboxylic acid and of its cis-($\pm$) and trans-($\pm$) racemates is illustrated below.

EXAMPLE 1

Preparation of 4-Hydroxycyclohexyl 1-Isopropyl-9,10-dihydrolysergate

A reaction mixture was prepared from 9.36 g of 1-isopropyl-9,10-dihydrolysergic acid, 20 g of cyclohexane-1,4-diol and 5.7 g of p-toluenesulfonic acid. The reaction mixture was heated overnight at about 90° C. and was then cooled. The reaction mixture was partitioned between 400 ml of ethylene dichloride and 250 ml of water, the pH being adjusted to about 11 with concentrated ammonium hydroxide. The organic layer was washed with 200 ml of 10% hydrochloric acid followed by 200 ml of water. The organic layer was separated and evaporated to dryness in vacuo, to leave 4-hydroxycyclohexyl 1-isopropyl-9,10-dihydrolysergate hydrochloride formed in the above reaction and workup, as a residue. The hydrochloride salt crystallized and the crystalline salt was separated by filtration: yield=about 2.3 g (17%); nmr indicated it was a mixture of cis and trans isomers; molecular ion of free base at 410.

Following the above procedure 3.12 g of 1-isopropyl-9,10-dihydrolysergic acid, 4.64 g of purified trans-cyclohexane-1,4-diol and 1.9 g of p-toluene sulfonic acid were heated together at 110° C. overnight. The reaction mixture was cooled and the cooled mixture partitioned between the ethylene dichloride and water at pH=about 10. The organic layer was separated and the separated layer washed with 250 ml of 10% hydrochloric acid. The hydrochloric acid salt was recovered by filtration, but crystallized with difficulty from a methanol/ether solvent mixture. The organic filtrate was concentrated, and the residue dissolved in ethylene dichloride. The hydrochloride salt fractions were combined in aqueous solution, which was contacted with dilute ammonium hydroxide to convert the hydrochloride salt to the free base. The free base was extracted into (CH$_2$Cl)$_2$ and purified. The free base was then converted to the maleate salt of trans-4-hydroxycyclohexyl 1-isopropyl-9,10-dihydrolysergate which was recrystallized from an ethanol/ether solvent mixture; molecular ion at 410; yield=0.43 g.

Analysis: Calc.: C, 66.14; H, 7.27; N, 5.23; Found: C, 65.98; H, 7.06; N, 5.17.

Following the above procedure, 3.12 g of 1-isopropyl-9,10-dihydrolysergic acid and 5.5 g of ciscyclohexane-1,4-diol were reacted in the presence of 1.9 g of p-toluenesulfonic acid by heating at about 90° C. for 18 hours. The reaction mixture was worked up as above and the solvent evaporated to dryness to yield the free base of cis-($\pm$)-4-hydroxycyclohexyl 1-isopropyl-9,10-dihydrolysergate. The free base was converted to the maleate salt and the maleate salt crystallized from a mixture of methanol and ether to yield a tan colored solid. Two more recrystallizations followed by a charcoal decolorization yielded 1.3 g of cis-4-hydroxycyclohexyl-1-isopropyl-9,10-dihydrolysergate maleate; yield=1.3 g; molecular ion at 410.

The intermediate cis and trans-cyclohexane-1,4-diols were prepared as follows:

PREPARATION I

A reaction mixture containing 23.2 g of cyclohexane-1,4-diol (estimated to be a 50/50 mixture of the cis and trans isomers) and 20.4 g of n-butyl-boronic acid was prepared in 300 ml of toluene. The reaction mixture was heated to reflux temperature overnight using a Dean-Stark trap. The reaction mixture was concentrated in vacuo to give a mixture of the cis isomer as the boronic acid ester and the unreacted trans isomer. The cis conformation only of the two cyclohexane-1,4-diols will form a diester with n-butylboronic acid. The trans isomer will not react because the resulting diester would be too strained to form a five-membered ring. The n-butyl boronic ester distilled at 65°-74° C. at 0.1 torr. 10 ml of ethylene glycol were added to the distillate which was heated at about 80° C. for an hour to displace the boronic ester grouping from the cis-cyclohexane-1,4-diol. The n-butylboronic ethylene glycol was removed by distillation at 35°-80° C. at 3-8 torr. The residue comprising cis-cyclohexane-1,4-diol was recrystallized from ethyl acetate. Yield=1.44 g.

The structure was confirmed by 360 MH$_z$ nmr.

The trans-isomer was prepared by adding 10 ml of ethylene glycol to the residue remaining after distillation of the boronic ester cis isomer. The mixture was allowed to sit for about 1 hour at which time the boronic ester of ethylene glycol was removed by distillation at about 35° C. at 3 torr. The hot residue consisting of trans-cyclohexane-1,4-diol was recrystallized from ethyl acetate; yield=5.2 g. Again, the trans structure was confirmed by 360 MH$_z$ nmr.

The novel method of this invention whereby 5HT receptors are blocked but alpha receptors are not affected at a given dose level is potentially useful in treating disease states in which an excess of circulating serotonin is a major cause. These disease states include hypertension, thrombosis, anorexia nervosa, depression, mania, carcinoid syndrome, migraine and vasospasm. The lack of alpha receptor inhibitory activity indicates that the usual undesirable side affects associated with alpha receptor blockade—postural hypotension, tachycardia, impotence, and increased plasma renin levels—will not accompany the use of a compound according to formula I in treating hypertension, etc. in contrast to many presently available hypotensive agents including ketanserin.

Compounds according to formula I have an extremely high affinity for 5HT$_2$ receptors, with a much lower affinity for alpha receptors. Ratios of relative dissociation constants for interaction with alpha to 5HT$_2$ receptors are of the order of 200,000–300,000 indicating dramatic selectivity for 5HT$_2$ receptors. The apparent dissociation constants (K$_B$) are a measure of affinity for 5HT$_2$ and alpha receptors and are expressed as the negative logarithm and are determined according to the following protocol.

Male Wistar rats (150–300 gram weight) were killed and their external jugular veins and thoracic aortas dissected free of connective tissue, cannulated in situ and placed in a modified Krebs' bicarbonate buffer in a suitable tissue bath. Two L-shaped 30-gauge stainless-steel hypodermic needles were inserted in each cannula and the dissected vessels gently pushed onto the needles. One needle was attached with thread to a stationary glass rod and the other to the transducer. [The procedure employed was that described by Hooker, Calkins and Fleisch, *Blood Vessels*, 14, 1, (1977) for use with circular smooth muscle preparations.]

The modified Krebs' bicarbonate buffer had the following makeup: (concentrations in millimoles): sodium chloride, 118.2; potassium chloride, 4.6; calcium chloride dihydrate, 1.6; potassium dihydrogenphosphate, 1.2; magnesium sulfate, 1.2; dextrose, 10.0; sodium bicarbonate, 24.8; and water q.s. to 1000 g. The tissue baths were maintained at 37° C. and were aerated with 95% oxygen-5% CO$_2$. An initial optimum resting force of 1 and 4 g was applied to the jugular vein and aorta, respectively. Isometric contractions were recorded as changes in grams of force on a Beckman Dynograph with Statham UC-3 transducers and microscale accessory attachment. Tissues were allowed to equilibrate 1 to 2 hours before exposure to drugs. Control responses to serotonin in the jugular vein and to norepinephrine in the aorta were obtained. The vessels were then incubated with appropriate concentrations of antagonist for one hour. Responses to serotonin or to norepinephrine were then repeated in the presence of the antagonist. Contraction to serotonin was evaluated in the jugular vein since this tissue produces marked responses to serotonin in the absence of alpha receptors—see Cohen and Wiley, *J. Pharm. Exp. Ther.*, 205, 400 (1978) and Cohen, Colbert and Wittenauer, *Drug Dev. Res.*, 5 513 (1985) for descriptions of the procedures employed.

Alpha receptor antagonist activity was evaluated in the aorta ($\alpha_1$) or guinea pig ileum ($\alpha_2$).

Apparent antagonist dissociation constants were determined for each concentration of antagonist according to the following equation:

$$K_B = \frac{[B]}{[\text{dose ratio} - 1]}$$

wherein [B] is the concentration of the antagonist and the dose ratio is the ED$_{50}$ of the agonist in the presence of the antagonist divided by the control ED$_{50}$. These results are them expressed as the negative logarithm of K$_B$. The $-\log$ K$_B$ values obtained for 4-hydroxycyclohexyl 1-isopropyl-9,10-dihydrolysergate, isomer mixture (racemate) and pure isomers (cis and trans referring to stereochemistry of the hydroxycyclohexyl group) plus standard error against 5HT$_2$ receptors are given below in Table 1.

TABLE 1

| Compound | -Log K$_b$ ± S.E. |
|---|---|
| 4-hydroxycyclohexyl 1-isopropyl-9,10-dihydrolysergate | |
| mixture | 10.18 (±) 0.12 |
| cis | 9.95 (±) 0.13 |
| trans | 10.02 (±) 0.07 |

The lack of alpha blocking activity for compounds of formula I was demonstrated by the following experiment. The in vitro rat aorta preparation described above was used for $\alpha_1$-receptors and the guinea pig ileum for $\alpha_2$-receptors. ED$_{50}$ (median effective dose) for norepinephrine was determined in the presence of a 10$^{-5}$ molar dose of the test compound and this ED$_{50}$ compared to a control ED$_{50}$. The resulting dissociation constants are given in Table 2 below.

TABLE 2

| | -Log K$_b$ ± S.E. | |
|---|---|---|
| Compound | $\alpha_1$ | $\alpha_2$ |
| 4-hydroxycyclohexyl 1-isopropyl-9,10-dihydrolysergate | | |
| mixture | 4.84 ± 0.34 | 6.93 ± 0.22 |
| cis | 5.35 ± 0.33 | 6.81 ± 0.08 |
| trans | 5.71 ± 0.17 | 7.18 ± 0.18 |

None of the above compounds significantly antagonized alpha receptors at a 10$^{-6}$M dose.

The compounds of this invention also lack demonstrable effects against histamine or carbamyl choline (muscarinic) contraction in guinea pig trachea, using standard procedures.

TABLE 3

| | -Log K$_b$ ± S.E. | |
|---|---|---|
| Compound | Histamine | Muscarinic |
| 4-hydroxycyclohexyl 1-isopropyl-9,10-dihydrolysergate | | |
| Mixture | <5 | <5 |
| trans | <5 | <5 |

The specificity for 5HT$_2$ receptors compared to 5HT$_1$, receptors of compounds according to formula III above in rat cortical membranes is given in Table 4. The procedures employed are those set forth in Cohen, Colbert and Wittenauer (loc. cit.) for other tissues.

TABLE 4

| Compound | Rat Cortical Membrane Binding IC$_{50}$ (nM) | |
|---|---|---|
| | 5HT | 5HT$_2$ |
| 4-hydroxycyclohexyl 1-isopropyl-9,10-dihydrolysergate | | |
| mixture | 530 | 3 |
| trans | 390 | 0.7 |

In spontaneously hypertensive rats (SHR), in which blockade of alpha$_1$ receptors but not 5HT$_2$ receptors lowers blood pressure, there was no effect on blood pressure or heart rate upon oral administration of 4-hydroxycyclohexyl 1-isopropyl-9,10-dihydrolysergate at a 10 mg/kg dose.

The relative potency and selectivity of the cis and trans isomers and cis-trans isomer mixture of 4-hydroxycyclohexyl 1-isopropyl-9,10-dihydrolysergate for 5HT$_2$ and alpha$_2$ receptors was demonstrated in vivo in pithed SHR according to the following protocol.

SHR were anesthetized with halothane, femoral arterial and venous catheters were implanted as before and the trachea was cannulated. Each rat was pithed by passing a steel rod through the right orbit and down the entire length of the spinal column. The steel rod remained in place for the duration of the experiment. Immediately after pithing, the rats were ventilated with room air. An equilibration period of 15 minutes was observed prior to control measurements and administration of drugs or vehicle p.o. Increasing doses of serotonin or the alpha$_2$ agonist clonidine were injected i.v. one or six hours after oral treatment with the agonists. The response was recorded and the blood pressure allowed to recover to control levels after serotonin. Cumulative dose-response curves to clonidine were determined. The test drug solution was prepared fresh daily. Tables 5 and 6 give the results of these determinations at a dose level of 0.1 mg/kg.

TABLE 5

Relative Potency of Serotonin (5HT) Antagonists
One Hour After Oral Administration of 0.1 mg/kg
to Pithed Rats[a]

| Compound | 5HT Dose, mg/kg, iv[b] | Curve Shift Relative to trans |
|---|---|---|
| trans | 4000 | — |
| mixture | 1100 | 3.6 |
| cis | 345 | 11.6 |
| Vehicle | 9 | 444.4 |

[a]Conscious spontaneously hypertensive rats (SHR) were treated orally 1 hour before anesthesia, pithing and determination of pressor-dose response curves to multiple doses of 5HT iv (n= 4-10/group).
[b]Dose of 5HT required to increase mean arterial blood pressure by 50 mmHg.

TABLE 6

Relative Potency of Serotonin (5HT) Antagonists
Six Hours After Oral Administration of 0.1 mg/kg
to Pithed Rats[a]

| Compound | 5HT Dose, mg/kg, iv[b] | Curve Shift Relative to trans |
|---|---|---|
| trans | 680 | — |
| mixture | 123 | 5.5 |
| cis | 28 | 24.3 |
| Vehicle | 9 | 75.6 |

[a]Conscious spontaneously hypertensive rats (SHR) were treated orally 6 hours before anesthesia, pithing and determination of pressor-dose response curves to multiple doses of 5HT iv (n = 4-10/group).
[b]Dose of 5HT required to increase mean arterial blood pressure by 50 mmHg.

When a dose of 0.3 mg/kg po of cis-4-hydroxycyclohexyl 1-isopropyl-9,10-dihydrolysergate was given, the dose of 5HT required to increase mean arterial BP by 50 mmHg was 1800, giving a curve shift of 6.7. When a dose of 0.03 mg/kg po of trans-4-hydroxycyclohexyl 1-isopropyl-9,10-dihydrolysergate was given, the 5HT dose required to shift mean arterial BP 50 mmHg was 200 μg/kg, iv, indicating by extrapolation, that the trans isomer was 3X the cis isomer in potency.

The above differences in potency between the cis and trans isomers of 4-hydroxy cyclohexyl 1-isopropyl-9,10-dihydrolysergate when administered by the oral route were unexpected considering the in vitro data of Table 1 above.

The alpha$_2$ antagonist activity as determined in pithed SHR at a 100 mg/kg dose level po was slight for the isomer mixture and the individual isomers and showed a greater specificity (5HT$_2$ vs alpha$_2$) than the in vitro date of Table 1-2 indicated.

In humans and mammals other than SHR, hypertension may be mediated through 5HT$_2$ receptors. Thus, compounds of formula III would be expected to lower blood pressure in humans as does ketanserin, another 5HT$_2$ blocker, but without the side effects attributable to alpha adrenergic receptor blockade.

In carrying out our novel therapeutic process, a pharmaceutically-acceptable salt of a drug according to formula III above formed with a non-toxic acid is administered orally or parenterally to a mammal with an excess of circulatory serotonin in which it is desirable to block 5HT$_2$ receptors in order to alleviate symptoms attributable to excessive serotonin levels such as high blood pressure and migraines. For parenteral administration, a water soluble salt of the drug is dissolved in an isotonic salt solution and administered by the i.v. route. For oral administration, a pharmaceutically-acceptable salt of the drug is mixed with standard pharmaceutical excipients such as starch and loaded into capsules or made into tablets, each containing 0.1 to 100 mg of active drug. Dosage levels of from 0.1-10 mg/kg have been found to be effective in blocking 5HT$_2$ receptors. Thus, the oral dosage would be administered 2-4 times per day, giving a daily dosage range of about 0.003 to about 10.0 mg./kg. per day.

Other oral dosage forms, suspensions, elixirs and tablets, can also be utilized and are preparable by standard procedures.

We claim:

1. A method of blocking 5HT$_2$ receptors without effect on alpha receptors which comprises administering to a mammal having an excess of serotonin centrally or peripherally an 5HT$_2$ blocking dose which does not affect alpha receptors of an ergoline of the formula:

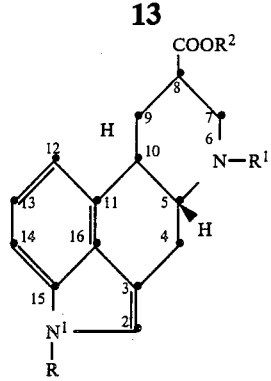

wherein R is primary or secondary $C_{1-8}$ alkyl, $CH_2C_{2-4}$ alkeny, $C_{3-8}$ cycloalkyl or $C_{3-6}$ cycloalkyl-substituted $C_{1-5}$ primary or secondary alkyl, the total number of carbon atoms in R not to exceed 8; $R^1$ is $C_{1-4}$ straight chain alkyl or allyl, and $R^2$ is hydroxy $C_{5-7}$ cycloalkyl, and pharmaceutically acceptable acid addition salts thereof.

2. A method according to claim 1 in which trans-4-hydroxycyclohexyl 1-isopropyl-9,10-dihydrolysergate is the drug employed.

* * * * *